United States Patent [19]
Kohayakawa

[11] Patent Number: 5,280,313
[45] Date of Patent: Jan. 18, 1994

[54] OPHTHALMIC MEASURING APPARATUS

[75] Inventor: Yoshimi Kohayakawa, Yokohama, Japan

[73] Assignee: Canon Kabushiki Kaisha, Tokyo, Japan

[21] Appl. No.: 917,429

[22] Filed: Jul. 23, 1992

[30] Foreign Application Priority Data

Jul. 25, 1991 [JP] Japan .................. 3-208496
Jan. 29, 1992 [JP] Japan .................. 4-038583

[51] Int. Cl.$^5$ ............................................. A61B 3/10
[52] U.S. Cl. ..................... 351/211; 351/206; 351/214
[58] Field of Search ............... 351/211, 212, 205, 206, 351/208, 214, 221, 222, 223, 243; 356/124, 128, 355, 357, 28.5

[56] References Cited

U.S. PATENT DOCUMENTS

| | | | |
|---|---|---|---|
| 4,372,655 | 2/1983 | Matsumura et al. | 351/206 |
| 4,402,601 | 9/1983 | Riva | 351/206 |
| 4,609,287 | 9/1986 | Kohayakawa | 356/124 |
| 4,697,895 | 10/1987 | Sekiguchi et al. | 351/243 |
| 4,755,041 | 7/1988 | Ishikawa et al. | 351/211 |
| 4,820,037 | 4/1989 | Kohayakawa et al. | 351/211 |
| 4,938,584 | 7/1990 | Suematsu et al. | 351/211 |

FOREIGN PATENT DOCUMENTS 59-149126  8/1984  Japan .
2-4310     1/1990  Japan .

*Primary Examiner*—Loha Ben
*Attorney, Agent, or Firm*—Fitzpatrick, Cella, Harper, & Scinto

[57] ABSTRACT

An ophthalmic measuring apparatus for easily determining whether an ametropia of an eye to be tested is caused by an abnormality in the length of the ocular axis or an abnormality in the lens or the cornea of the eye, includes a first light source, a first detector, and an ocular refractivity measuring unit for optically measuring the ocular refractivity of the eye. The apparatus further includes a second light source different from the first light source, the second detector different from the first detector, an ocular-axis-length measuring unit for optically measuring the length of the ocular axis of the eye, and a determination unit for determining the characteristics of the ametropia of the eye from the result of the measurement by the ocular refractivity measuring unit and the result of the measurement by the ocular-axis-length measuring unit.

7 Claims, 5 Drawing Sheets

OPHTHALMIC MEASURING APPARATUS

BACKGROUND OF THE INVENTION

1. Field of the Invention

This invention relates to an ophthalmic measuring apparatus which is widely utilized in ophthalmic hospitals or by opticians.

2. Description of the Related Art

Various methods of optically measuring the ocular refractivity of an eye have been known. Methods of optically measuring the length of the ocular axis of an eye have been known, in which, as described, for example, in Japanese Patent Application Public Disclosure (Kokai) No. 2-4310 (1990), a coherent light beam is projected along the ocular axis of an eye, and the length of the ocular axis is calculated from a change in the number of interference fringes formed by light beams reflected by the cornea and the fundus of the eye as a result of modulating the wavelength of the light beam emitted from the light source.

However, in the above-described conventional approach, it is impossible to identify whether an ametropia of an eye to be tested is axial, caused by an abnormality in the length of the ocular axis of the eye, or refractive, caused by an abnormality in the lens or the cornea of the eye.

SUMMARY OF THE INVENTION

It is an object of the present invention to overcome the axial deficiencies in the prior art.

It is another object of the present invention to provide an ophthalmic measuring apparatus which can identify whether an ametropia of the eye to be tested is axial, caused by an abnormality in the length of the ocular axis of the eye, or refractive, caused by an abnormality in the lens or the cornea of the eye, according to the measured refractivity and the measured length of the ocular axis.

According to one aspect, the present invention which achieves these objectives relates to an ophthalmic measuring apparatus comprising ocular refractivity measuring means for optically measuring the ocular refractivity of an eye to be tested, the ocular refractivity measuring means comprising a first light source and first detection means, and ocular-axis-length measuring means for optically measuring the length of the ocular axis of the eye. The ocular-axis-length measuring means comprises a second light source different from the first light source, and second detection means different from the first detection means.

The apparatus can further comprise determination means for determining whether an ametropia of the eye is axial, caused by an abnormality in the length of the ocular axis or refractive, caused by an abnormality in the lens or the cornea of the eye, from a result of the measurement by the ocular refractivity measuring means and a result of the measurement by the ocular-axis-length measuring means.

The ocular refractivity measuring means and the ocular-axis-length measuring means can simultaneously perform their measurements. In addition, the apparatus can further comprise a common optical system used by the ocular refractivity measuring means and the ocular-axis-length measuring means to perform their measuring operations.

The ocular-axis-length measuring means further comprises a projection optical system for projecting an intensity-modulated light beam emitted from the second light source onto the eye, and a light-receiving optical system for projecting a light beam obtained by synthesizing light beams reflected by the cornea and the fundus of the eye illuminated by the intensity-modulated light beam onto the second detection means. The ocular-axis-length measuring means comprises means for obtaining the length of the ocular axis using a detection signal representing the synthesized light beam from the second detection means. The ocular-axis-length measuring means further comprises a projection optical system for projecting a light beam emitted from the second light source onto the eye, a light-receiving optical system for projecting a light beam obtained by synthesizing light beams reflected by the cornea and the fundus of the eye illuminated by the light beam emitted from the second light source onto the second detection means, and a reference optical system for projecting a light beam emitted from the second light source onto two surfaces having a known distance therebetween and projecting a light beam obtained by synthesizing light beams reflected by the two surfaces onto third detection means different from the second detection means. The ocular-axis-length measuring means comprises means for obtaining the length of the ocular axis by comparing interference fringes detected by the second and third detection means when the wavelength of the light beam from the second light source changes.

The ocular refractivity measuring means further comprises a multi-aperture diaphragm for converting a light beam reflected by the fundus of the eye illuminated by the first light source into a plurality of spot light beams. The first detection means measures the ocular refractivity by detecting a plurality of spot light images formed by the plurality of spot light beams.

The foregoing and other objects, advantages and features of the present invention will become more apparent from the following description of preferred embodiments taken in conjunction with the accompanying drawings.

DESCRIPTION OF THE PREFERRED EMBODIMENTS

Preferred embodiments of the present invention will now be explained in detail with reference to the drawings.

Figure 1:
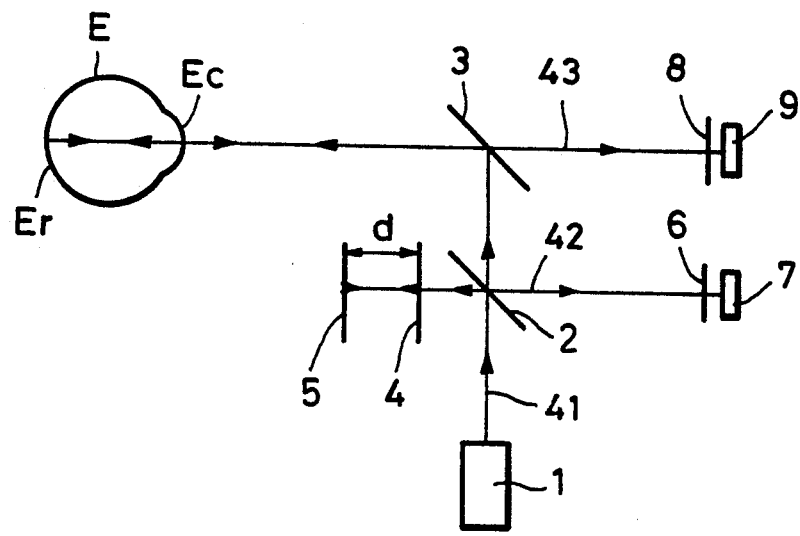
FIG. 1 is a diagram illustrating the principle of a system of measuring the length of the ocular axis of an eye.

Before explaining the operation and construction of the embodiments, an explanation will be provided of the principle of a system of measuring the length of the ocular axis of an eye with reference to FIG. 1. In FIG. 1, beam splitters 2 and 3 are provided along an optical path 41 from a light source 1 emitting a coherent and modulatable light beam to an eye E to be tested. A semitransparent first reference surface 4 and a second reference surface 5, separated by a distance d, are disposed along an optical path 42 orthogonal to the optical path 41 at the reflection side of the beam splitter 2. A diaphragm 6 and a photosensor 7 are disposed along the optical path 42 at the side opposite to the reference surfaces 4 and 5 with respect to the beam splitter 2. A diaphragm 8 and a photosensor 9 are disposed along an optical path 43 orthogonal to the optical path 41 at the transmission side of the beam splitter 3 at the side opposite to the eye E.

In measuring the length of the ocular axis of the eye E, the coherent light beam emitted from the light source 1 is divided into a reflected component and a transmitted component by the beam splitter 2. The reflected component is reflected to the first reference surface 4. A part of the reflected component is reflected by the first reference surface 4, and the remainder of the reflected component is reflected by the second reference surface 5. The two reflected light beams interfere with each other, and are sensed by the photosensor 6 after passing through the diaphragm 6. The transmitted component is reflected in the direction of the eye E by the beam splitter 3, is further reflected by the cornea Ec and the fundus Er of the eye E. The two reflected light beams interfere with each other, and are sensed by the photosensor 9 after passing through the beam splitter 3 and the diaphragm 8.

If the wavelength of the light beam from the light source 1 changes as a result of modulating the light beam 1 with voltage or the like, interference fringes change in accordance with the change in the wavelength, thereby changing the intensities of signals generated by the photosensors 7 and 9. Since the distance d between the reference surfaces 4 and 5 is previously known, the length of the ocular axis between the cornea Ec and the fundus Er can be obtained from the ratio of the numbers of fringes sensed by the photosensors 7 and 9 and the distance d. In this method, it is possible to obtain the length of the ocular axis even if the exact wavelength of the light beam emitted from the light source 1 is not known.

Figure 2:
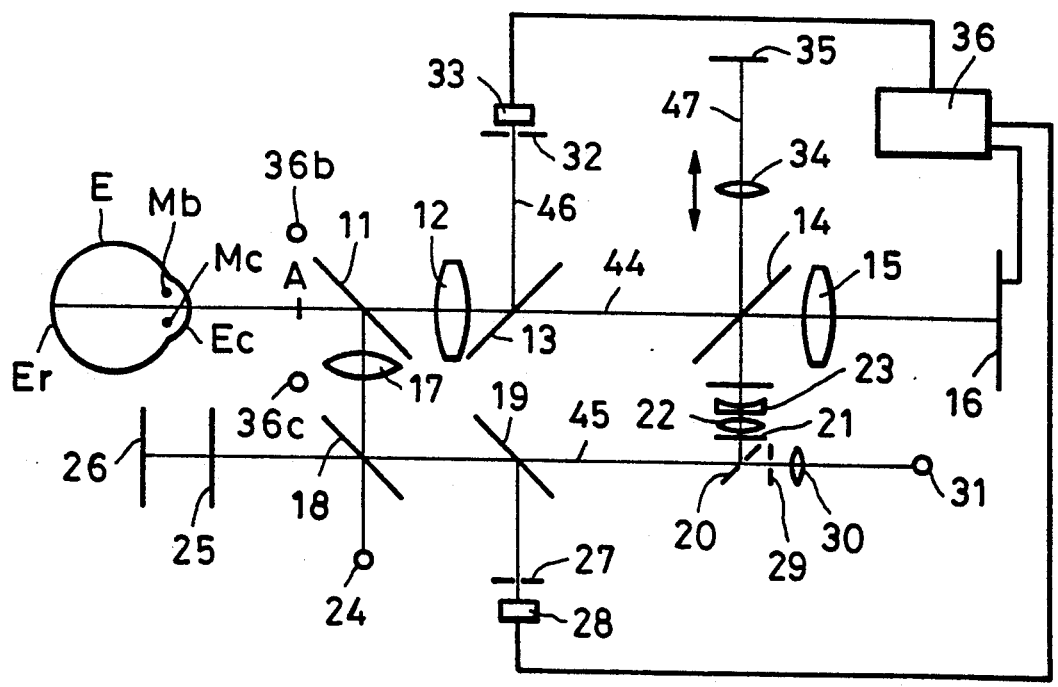
FIG. 2 is a diagram showing the configuration of a first embodiment of the present invention.

FIG. 2 is a diagram showing the configuration of a first embodiment, which is provided with the functions of measuring the refractivity of the eye, the curvature of the cornea, and the length of the ocular axis of an eye to be tested. A beam splitter 11, a lens 12, beam splitters 13 and 14, a lens 15 and a CCD (charge-coupled device) image pickup device 16 are arranged along an optical path 44 linearly extending from an eye E to be tested from the eye E to device 16. The directions in which the reflecting surfaces of the beam splitters 11 and 14 extend are symmetrical with respect to a line orthogonal to path 44. A detouring optical path 45 from the beam splitter 11 to the beam splitter 14 is provided with some reflecting surfaces. Accordingly, the light beam from the eye E is incident upon the image pickup device 16 after passing through the two optical paths 44 and 45, respectively.

Figure 3:
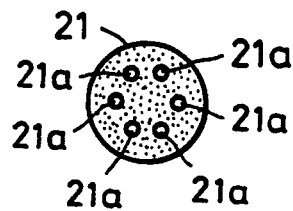
FIG. 3 is a front view of a six-aperture diaphragm.
Figure 4:
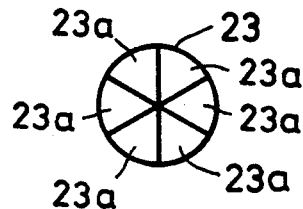
FIG. 4 is a front view of a wedge prism.
Figure 5:
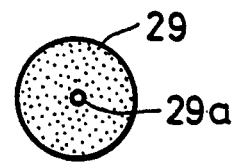
FIG. 5 is a front view of another diaphragm.

That is, a lens 17, beam splitters 18 and 19, a perforated mirror 20, a six-aperture diaphragm 21 in which six small apertures 21a are provided so as to form an equilateral hexagon, as shown in FIG. 3, a lens 22, and a prism 23 comprising six divided wedge prisms 23a corresponding to the six small apertures 21a, as shown in FIG. 4, are sequentially arranged from the beam splitter 11 to the beam splitter 14 along the optical path 45. A coherent light source 24 generating a modulatable outgoing light beam for measuring the length of the ocular axis of the eye is provided in the direction of transmission of the beam splitter 18. Reference surfaces 25 and 26 with a known interval d therebetween are disposed at the side opposite to the beam splitter 19 with respect to the beam splitter 18. A diaphragm 29 provided with a small aperture 29a in its center, as shown in FIG. 5, a lens 30, and a light source 31 for measuring the refractivity of the eye are arranged behind the aperture of the perforated aperture 20. A diaphragm 27 and a photosensor 28, serving as a reference photosensor corresponding to the photosensor 7 shown in FIG. 1, are also provided.

Figure 6:
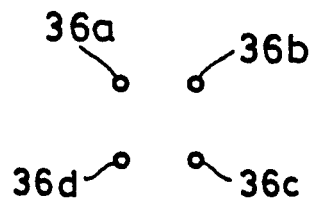
FIG. 6 is a schematic diagram showing the arrangement of light sources for illuminating a front portion of an eye.

A diaphragm 32 and a photosensor 33 for measuring the length of the ocular axis of the eye, corresponding to the photosensor 9 shown in FIG. 1, are provided along an optical path 46 in the direction of reflection of the beam splitter 13. An adjustable diopter lens 34 and a viewing point guiding target 35 are provided along an optical path 47 provided in the direction of reflection of the beam splitter 14. FIG. 6 is a vertical cross-sectional view of a surface "A" provided between the beam splitter 11 and the eye E along the optical path 44. Four light sources 36a–36d for illuminating a front portion of the eye E are arranged on the surface "A" symmetrically with respect to the optical path 44. The outputs of the photosensors 28 and 33 and the image pickup device 16 are connected to a calculation unit 36 which includes a CPU (central processing unit) and the like. The calculation unit 36 determines whether an ametropia of the eye E is axial, caused by an abnormality in the length of the ocular axis or refractive, based on the measured refractivity and the measured length of the ocular axis.

In measuring the length of the ocular axis, the line of sight of the individual having the eye E is guided by the visual point guiding target 35 so that the eye E is always directed in a fixed direction. Since respective individuals have eyes of different diopters, the vision of the individual having the eye E is appropriately corrected so that the individual can clearly see the visual point guiding target 35 using the diopter lens 34, and measurement is performed in this state.

In measuring the length of the ocular axis, the light source 24 is lit, and the light beam emitted from the light source 24 passing through the beam splitter 18 and the lens 17 is reflected by the beam splitter 11 in the direction of the eye E. A part of the light beam reaching the eye E is reflected by the fundus Er of the eye E, and the remainder of the light beam is reflected by the cornea Ec of the eye E. The two light beams reflected by the fundus Er and the cornea Ec return along the optical path 44, are reflected by the beam splitter 13 after passing through the beam splitter 11 and the lens 12, and are incident upon the photosensor 33 after passing through the diaphragm 32. The calculation unit 36 calculates the length of the ocular axis by comparing the signal obtained from the photosensor 33 with the signal obtained from the photosensor 28 by referring to the reference surfaces 25 and 26. That is, the length of the ocular axis can be measured from the ratio of the number of fringes detected by the photosensors 28 and 33, and the known interval d between the reference surfaces 25 and 26.

Figure 7:
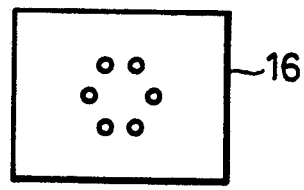
FIG. 7 is a schematic diagram illustrating images of a fundus, composed of light reflected by the fundus, on an image pickup device.

In measuring the ocular refractivity, the light source 31 is first lit. The light beam from the light source 31 passing through the lens 30, the diaphragm 29, the perforated mirror 20, the beam splitters 19 and 18, the lens 17 and the beam splitter 11 projects an image of the light source onto the fundus Er of the eye E. The light beam reflected by the fundus Er returns along the original optical path, is reflected by the perforated mirror 20, and is divided into six spot light beams by the six-aperture diaphragm 21. The six spot light beams pass through lens 22 and are spread by the wedge prism 23, are reflected by the beam splitter 14, pass through lens 15, and are incident upon the image pickup device 16. As shown in FIG. 7, six spot light images are formed on the image pickup device 16. Since a change in the degree of refraction is reflected as a change in the distance of each image from the center, the value of the refractivity can be obtained by calculating the position of the spot light image by the calculation unit 36.

In measuring the curvature of the cornea, the four light sources 36a–36d in front of the eye E are lit, and four images Ma–Md of the cornea, composed of light reflected by the cornea, are formed on the cornea Ec. The images Ma–Md of the cornea, composed of light reflected by the cornea, are focused on the image pickup device 16 by the lenses 12 and 15 provided along the optical path 44. Since the distance of each focused image from the center depends on the curvature of the cornea Ec, the curvature of the cornea Ec can be calculated by the calculation unit 36.

In the series of the above-described measuring operations, since the value of the refractivity changes in accordance with adjustment of the eye E, it is desirable to substantially simultaneously measure the refractivity and the length of the ocular axis. The present embodiment, which uses the same optical system for the two types of measurement and performs measurement from the same axial direction, can perform simultaneous measurement, and can identify whether an ametropia of an eye to be tested is axial, caused by an abnormality in the length of the ocular axis of the eye, or refractive, caused by an abnormality in the lens or the cornea of the eye using the calculation unit 36.

In the present embodiment, by having a configuration such that the measurement of the refractivity of an eye to be tested and the measurement of the length of the ocular axis of the eye are performed by separate light sources and separate detection units, the measurement of the refractivity and the measurement of the length of the ocular axis can be independently performed.

As a modification of the present embodiment, the calculation unit 36 may first measure the ocular refractivity, and calculate the conjugate position of the fundus in the optical system comprising the beam splitter 11, the lens 12 and the beam splitter 13 according to the measured value, position the diaphragm 32 and the photosensor 33 at the conjugate position using a driving system (not shown), and measure the length of the ocular axis. In this case, since a greater amount of light reflected by the fundus can be received in the photosensor 9 so as to be in better balance with the amount of light reflected by the cornea, accuracy in the measurement of the length of the ocular axis is increased.

The following ophthalmic apparatus according to a second embodiment of the present invention is used for measuring the length of the ocular axis of an eye to be tested. The apparatus comprises a projection system for projecting an incident light beam subjected to intensity modification onto the eye, a photosensing system for sensing a light beam obtained by synthesizing light beams reflected by the cornea and the fundus of the eye, and measuring means for obtaining the length of the ocular axis of the eye from the intensity distribution of a photosensing signal representing the synthesized light beam in the photosensing system.

The opthalmic apparatus having the above-described configuration calculates the length of the ocular axis of the eye by analyzing the intensity distribution of the photosensing signal.

The present embodiment will now be explained in detail with reference to the drawings.

Figure 8:
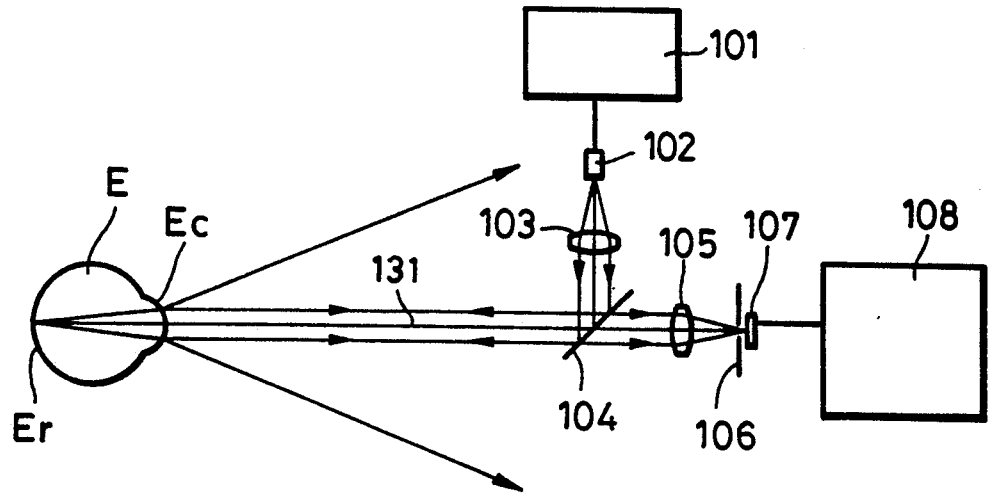
FIG. 8 is a diagram illustrating the principle of a system of measuring the length of the ocular axis of an eye according to a second embodiment of the present invention.

FIG. 8 is a diagram illustrating the principle of the ocular axis measuring system of the ophthalmic apparatus of the second embodiment. In FIG. 8, A lens 103 for making a light beam parallel, and a light dividing member 104 are arranged along an optical path 131 from a light source 102, such as a laser diode or the like, whose light intensity is modified by a power supply 101, to an eye E to be tested. An imaging lens 105 for imaging a light beam reflected by the eye E, and a diaphragm 106 and a photodiode 107 arranged at a position conjugate to the fundus Er of the eye E with respect to the imaging lens 105 are disposed behind the light dividing member 104. The signal from the photodiode 107 is processed by a signal processor 108.

The light beam emitted from the light source 102 which is subjected to intensity modification at a frequency of about 500 MHz (megahertz)–1 GHz (gigahertz) passes through the lens 103, is reflected by the light dividing member 104, and reaches the eye E. A part of the light beam is subjected to mirror-reflection by the cornea Ec of the eye E, and the remainder of the light beam reaches the fundus Er, where it is scattered. A part of the scattered light passes through the light dividing member 104 and the imaging lens 105 together with the light reflected by the cornea, and is sensed by the photodiode 107.

Figure 9A:
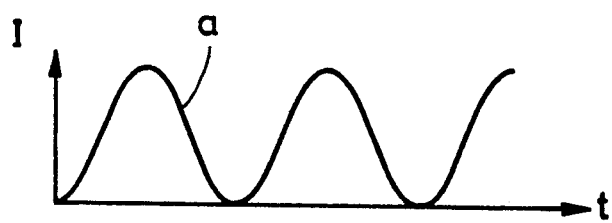
FIGS. 9(a)–9(c) are diagrams illustrating a signal subjected to intensity modulation over time.
Figure 9B:
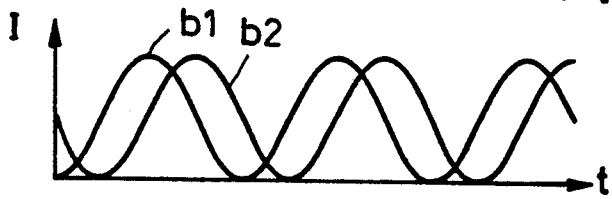
Figure 9C:
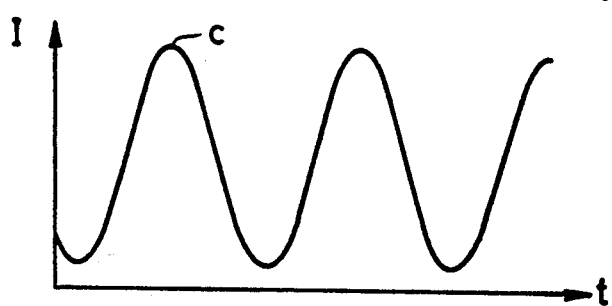

FIGS. 9(a) through 9(c) are diagrams illustrating the relationship between the intensities I of modulated light "a", reflected light b and a photosensing signal c in the photodiode 107, and time t, respectively, where the ordinate represents the intensity I, and the abscissa represents time t. The modulated light "a" emitted from the light source 102 is modulated so that its intensity changes sinusoidally, as shown in FIG. 9(a). The light b reflected by the eye E comprises light b1 reflected by the cornea Ec and light b2 reflected by the fundus Er. Since the optical path of the light b2 reflected by the fundus is longer than the optical path of the light b1 reflected by the cornea by twice the length of the ocular axis which is the distance between the cornea Ec and the fundus Er, the phase of the light b2 reflected by the fundus lags light b1 as shown in FIG. 9(b). The photosensing signal c of the photodiode 107 represents a light beam obtained by synthesizing the two reflected light beams, as shown in FIG. 9(c). Since the phase of this synthesized light beam depends on the phase difference between the two reflected light beams, the length of the ocular axis can be calculated from phase information on the synthesized light beam.

Figure 10:
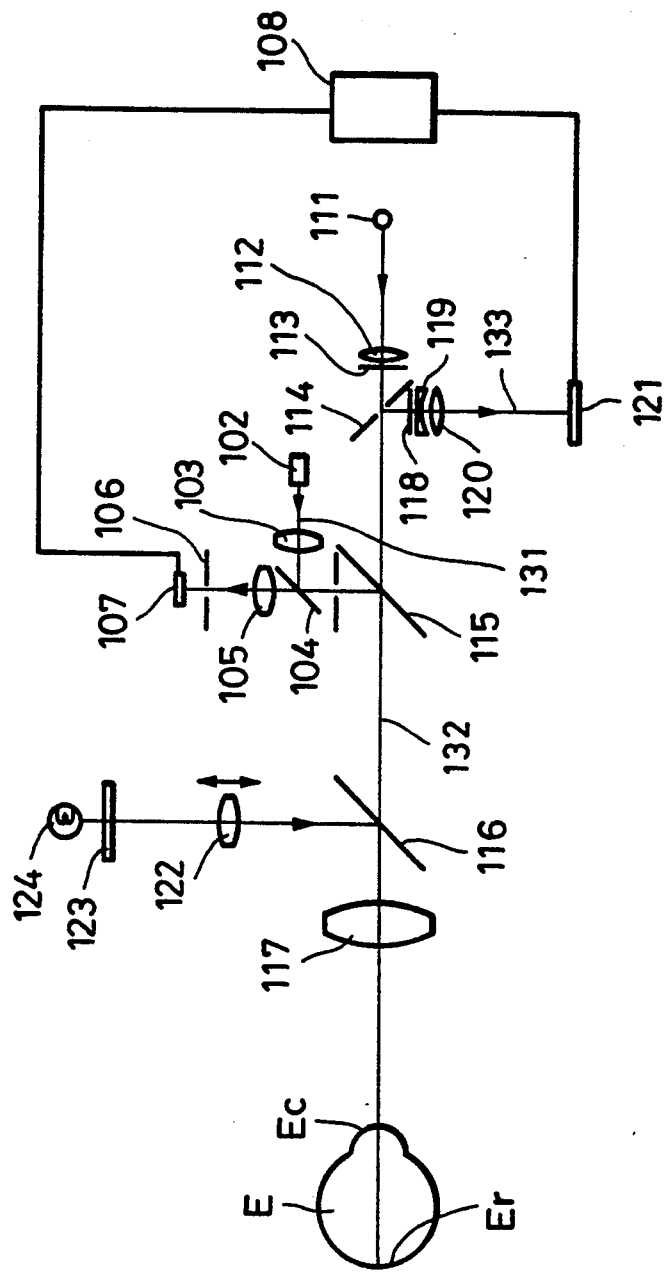
FIG. 10 is a diagram showing the configuration of a second embodiment of the present invention.

FIG. 10 is a diagram showing the configuration of a second embodiment of the present invention in which the above-described system for measuring the length of the ocular axis is incorporated in a refractometer. In FIG. 10, the same components as those shown in FIG. 8 are indicated by the same reference numerals. A lens 112, a diaphragm 113 having a central aperture disposed at a position conjugate to the position of the pupil of an eye E to be tested, a perforated mirror 114, light dividing members 115 and 116, and an objective lens 117 are arranged along an optical path 132 from a light source 111 to the eye E. A six-aperture diaphragm 118 having six apertures provided at a position substantially conjugate to the pupil of the eye E, a wedge prism 119 comprising six small prisms, an imaging lens 120 and a photosensor 121 are sequentially arranged along an optical path 133 in the direction of reflection of the perforated mirror 114. The value of the refractivity of the eye E is obtained from the positions of six photosensed light beams. A unit for measuring the length of the ocular axis of the eye based on the principle shown in FIG. 8 is disposed in the direction of reflection of the light dividing member 115 and comprises elements 102–108 as discussed with reference to FIG. 8. A visual target system comprising a diopter lens 122 movable in the direction of the optical path 132, a diopter guiding target 123 and a background light source 124 are disposed in the direction of reflection of the light dividing member 116.

When the individual having the eye E is situated at a predetermined position, the background light source 124 is lit, and the diopter lens 122 is operated in accordance with the diopter of the eye of the individual. When the light source 102 is lit, the light beam from the light source 102 is reflected by the light dividing members 104 and 115, and reaches the eye E after passing through the light dividing member 116 and the objective lens 117. Light beams reflected by the fundus Er and the cornea Ec of the eye E are sensed by the photodiode 107 after passing through the objective lens 117, the light dividing member 115, the light dividing member 104, the imaging lens 105 and the diaphragm 106. The length of the ocular axis of the eye E is measured in the same manner as described with reference to FIG. 8.

When the light source 111 is lit, the light beam from the light source 111 passes along the optical path 132, and reaches the eye E. A light beam reflected by the fundus Er of the eye E returns along the optical path 132, is reflected by the perforated mirror 114 to enter the optical path 133, and passes through the six-aperture diaphragm 118, the wedge prism 119 and the imaging lens 120. Six images of the fundus, composed of light reflected by the fundus, are formed on the photosensor 121. The signal processor 108 obtains the value of the refractivity of the eye E from the positional relationship among the images of the fundus on the photosensor 121. In this case, since the length of the ocular axis and the refractivity of the eye can be simultaneously measured, it is possible to evaluate and analyze the value of the refractivity of the eye by dividing it into an ocular-axis element and a refractive element.

As explained above, in the second embodiment, since the ophthalmic apparatus obtains the length of the ocular axis from a difference in the intensity of a signal representing the modulated light beam, it is possible to measure the length of the ocular axis even without using a coherent light beam. Furthermore, since measurement is performed in a non-contact state, there is no danger to the patient in performing this measurement.

As a modification of the second embodiment, the signal processor 108 may first measure the ocular refractivity, and measure the length of the ocular axis after positioning the diaphragm 106 and the photodiode 107 with a driving system (not shown) at a position conjugate to the fundus obtained from the measurement of the ocular refractivity.

As explained above, the ophthalmic measuring apparatus of the present invention can simply identify whether an ametropia of an eye to be tested is axial or refractive.

The individual components represented by the blocks shown in FIGS. 1, 2, 8 and 10 are well known in the ophthalmic measuring apparatus art and their specific construction and operation is not critical to the invention or the best mode for carrying out the invention. Moreover, the steps discussed in the specification for carrying out the invention can be easily programmed into well-known apparatus by those of ordinary skill in the art and since such programming per se is not part of the invention, no further description thereof is deemed necessary.

What is claimed is:

1. An ophthalmic measuring apparatus, comprising:
   ocular refractivity measuring means for optically measuring the ocular refractivity of an eye to be tested, said ocular refractivity measuring means comprising a first light source and first detection means; and
   ocular-axis-length measuring means for optically measuring the length of the ocular axis of the eye, said ocular-axis-length measuring means comprising a second light source different from said first light source, and second detection means different from said first detection means.

2. An apparatus according to claim 1, further comprising determination means for determining whether an ametropia of the eye is axial, caused by an abnormality in the length of the ocular axis, or refractive, caused by an abnormality in the lens or the cornea of the eye, from a result of the measurement by said ocular refractivity measuring means and a result of the measurement by said ocular-axis-length measuring means.

3. An apparatus according to claim 1, wherein said ocular refractivity measuring means and said ocular-axis-length measuring means simultaneously perform measurement.

4. An apparatus according to claim 1, further comprising a common optical system used by said ocular refractivity measuring means and said ocular-axis-length measuring means to perform their measuring operations.

5. An apparatus according to claim 1, wherein said ocular-axis-length measuring means further comprises a projection optical system for projecting an intensity-modulated light beam emitted from said second light source onto the eye, and a light-receiving optical system for projecting a light beam obtained by synthesizing light beams reflected by the cornea and the fundus of the eye illuminated by the intensity-modulated light beam onto said second detection means, and wherein said ocular-axis-length measuring means comprises means for obtaining the length of the ocular axis using a detection signal representing the synthesized light beam from said second detection means.

6. An apparatus according to claim 1, wherein said ocular-axis-length measuring means further comprises a projection optical system for projecting a light beam emitted from said second light source onto the eye, a light-receiving optical system for projecting a light beam obtained by synthesizing light beams reflected by the cornea and the fundus of the eye illuminated by said light beam emitted from said second light source onto said second detection means, and a reference optical system for projecting the light beam emitted from said second light source onto two surfaces having a known interval therebetween and projecting a light beam obtained by synthesizing light beams reflected by the two surfaces onto a third detection means different from said second detection means, and wherein said ocular-axis-length measuring means comprises means for obtaining the length of the ocular axis by comparing interference fringes detected by said second and third detection means when the wavelength of the light beam from said second light source changes.

7. An apparatus according to claim 1, wherein said ocular refractivity measuring means further comprises a multi-aperture diaphragm for converting a light beam reflected by the fundus of the eye illuminated by said first light source into a plurality of spot light beams, and wherein said first detection means measures the ocular refractivity by detecting a plurality of spot light images formed by said plurality of spot light beams.

* * * * *

UNITED STATES PATENT AND TRADEMARK OFFICE
CERTIFICATE OF CORRECTION

PATENT NO. : 5,280,313
DATED : January 18, 1994
INVENTOR(S) : YOSHIMI KOHAYAKAWA It is certified that error appears in the above-indentified patent and that said Letters Patent is hereby corrected as shown below:

ON THE COVER PAGE
    AT [57] Abstract
    line 9, "the second" should read --a second--.

COLUMN 1
    line 55, "axis" should read --axis,--.

COLUMN 2
    line 10, "means.  The" should read --means.  ¶ The--.

COLUMN 3
    line 34, "photosensor 6" should read --photosensor 7--.

COLUMN 4
    line 23, "perforated aperture 20." should read --perforated mirror 20.--.
    line 45, "axis" should read --axis,--.

COLUMN 6
    line 63, "lags" should read --lags behind--.

Signed and Sealed this

Twentieth Day of September, 1994

Attest:

BRUCE LEHMAN

*Attesting Officer*     *Commissioner of Patents and Trademarks*